United States Patent [19]

Shlain

[11] Patent Number: 5,382,231
[45] Date of Patent: Jan. 17, 1995

[54] METHOD FOR TRANSESOPHAGEAL RETRACTION OF THE STOMACH

[76] Inventor: Leonard M. Shlain, 40 Century Dr., Mill Valley, Calif. 94941

[21] Appl. No.: 12,219

[22] Filed: Feb. 2, 1993

[51] Int. Cl.$^6$ ............................................. A61M 31/00
[52] U.S. Cl. ...................................... 604/49; 128/898
[58] Field of Search .................... 604/26, 49, 50, 51; 128/898, DIG. 12, DIG. 13

[56] References Cited

U.S. PATENT DOCUMENTS

| | | |
|---|---|---|
| 4,133,315 | 1/1979 | Berman et al. |
| 4,311,146 | 1/1982 | Wonder |
| 4,341,218 | 7/1982 | Ü |
| 4,485,805 | 12/1984 | Foster, Jr. |
| 4,501,264 | 2/1985 | Rockey |
| 4,517,979 | 5/1985 | Pecenka |
| 4,648,383 | 3/1987 | Angelchik |
| 4,769,014 | 9/1988 | Russo |
| B1 4,769,014 | 2/1990 | Russo |
| 5,013,294 | 5/1991 | Baier ..................... 604/26 |
| 5,112,310 | 5/1992 | Grobe ..................... 604/49 |
| 5,139,478 | 8/1992 | Koninckx et al. ........ 604/26 |
| 5,151,086 | 9/1992 | Duh et al. ................ 604/51 |

*Primary Examiner*—Jerome L. Kruter
*Attorney, Agent, or Firm*—Townsend and Townsend Khourie and Crew

[57] ABSTRACT

A device for transesophageal stomach retraction comprises an elongate shaft having a proximal handle in a distal length. The distal length is deformable so that it can assume a desired configuration, such as a J-shaped curvature, and is deflectable so that it may be repositioned within the stomach. The proximal length may further include vacuum ports which permit the stomach to be drained and collapsed on the distal length to enhance contact. [This way, the] The treating physician inserts the device through the mouth of the patient with the distal length penetrating the stomach. Thereafter, the device is moved from the proximal end to manipulate the distal ends to move the stomach. Preferably, the device is deformed prior to such moving into a desired curvature, preferably a J-shaped configuration. The vacuum ports are utilized to draw the stomach over the device. Thereafter by exerting torque through the esophagus, the physician can manipulate and retract a patient's stomach from the inside permitting operation on the outside of the stomach and adjacent organs that require retraction of the stomach over extended periods of time, [during a variety of surgical procedures,] including both laparoscopic and open surgical procedures.

8 Claims, 11 Drawing Sheets y a pull wire. The means for increasing the cross-sectional area of the proximal length may be an inflatable balloon, a mechanically expansible cage, or the like. The means for selectively articulating the distal length of the shaft will usually be one or more control wires which are attached at or near a distal end of the shaft.

METHOD FOR TRANSESOPHAGEAL RETRACTION OF THE STOMACH

BACKGROUND OF THE INVENTION

1. Field of the Invention

The present invention relates generally to minimally invasive surgical methods and procedures. More particularly, the present invention relates to a transesophageal device which is used to retract a patient's stomach during the performance of a variety of laparoscopic and other surgical procedures.

Over the last several years, minimally invasive surgical procedures have become a viable alternative for a variety of open surgical procedures. Such minimally invasive procedures rely on introducing a viewing scope into the interior of a patient's body and performing the procedure using miniaturized instruments introduced through small incisions while observing the procedure on a video monitor. In this way, trauma to the patient and recovery times can be greatly reduced.

Of particular interest to the present invention, laparoscopic surgical procedures can be performed inside a patient's abdominal cavity by insufflating $CO_2$ gas (applying positive pressure) in the abdomen in order to raise the abdominal wall over the peritoneum, thus providing a working space. A laparoscope and various miniaturized surgical instruments can then be introduced into the working space through trocars (which are small valved tubes) which pass through small incisions made in the abdominal wall. Laparoscopic gall bladder removal, referred to as laparoscopic cholecystectomy, is becoming commonly practiced, and other laparoscopic procedures are being devised and contemplated.

Many laparoscopic procedures will require stomach retraction in order to gain access to desired target locations in the abdomen. In open surgical procedures, stomach retraction is relatively simple since surgeons can manually grasp the stomach with their hands and manipulate it as required by the procedure. In order to perform stomach retraction in laparoscopic procedures, a variety of clamps and clamp manipulation devices have been designed. Such devices are inserted through the trocars and are used to externally grasp the stomach and pull the stomach in the desired direction. Though workable, the use of such clamps is traumatic, frequently causing hematoma to the stomach wall, lacerations of the stomach surface, and occasionally puncturing the stomach wall. Such punctures can cause leaks and lead to peritonitis. Moreover, the use of such external clamps requires additional incisions through the abdominal wall increasing the number of trocars in order to accommodate one or more of the clamps to provide a desired retraction.

For these reasons, it would be desirable to provide alternative methods and devices for retracting the patient's stomach during laparoscopic and other surgical procedures. It would be particularly desirable if the methods and devices caused minimal or no trauma to the stomach and did not require access penetrations through the abdominal wall. Such methods and devices should preferably be introduced through the esophagus after the induction of anesthesia and permit retraction of the stomach by manipulation of controls affixed to the proximal end of the device which lies externally to the patient. The devices and methods should further provide for a wide degree of motion within the stomach in order to selectively retract an exposed portion of the external stomach to the laparoscopic viewing field.

2. Description of the Background Art

Transesophageal devices for treating obesity comprising a flexible tube and various structures at the distal end of the flexible tubes are described in U.S. Pat. Nos. 4,133,315; 4,485,805; 4,501,264; and 4,648,383. A gastroenteric feeding tube is described in U.S. Pat. No. 4,769,014 and Reexamination Certificate B1 4,769,014. Detachable balloon catheters are described in U.S. Pat. Nos. 4,311,146; 4,341,218; and 4,517,979.

SUMMARY OF THE INVENTION

Methods and devices are provided for organ retraction during surgical procedures, particularly during laparoscopic stomach and retraction and other minimally invasive procedures but could also be used during open surgical procedures. The method comprises inserting a device through a patient's orifice, such as the mouth and esophagus so that a distal end of the device lies within the stomach while a proximal end of the device remains extended outward through the patient's mouth. The proximal end of the device may then be manipulated in order to move the distal end of the device and thereby retract the stomach or other organ in a desired direction. Usually, the cross-sectional area of the distal end of the device will be increased in order to maximize the contact area between the device and the inside surface of the stomach or other organ. In a preferred embodiment, a distal length of the device will be formable in situ into a reverse J-curvature which, when properly oriented, will by itself retract the stomach. The device and method of the present invention will be described in connection with the stomach, but it will be appreciated that the principles apply to any body organ having a natural orifice, or to which an orifice can be formed.

The method may further comprise applying a vacuum to a plurality of ports along the distal end of the device (usually after increasing the cross-sectional area), where the vacuum will empty fluid and air from the stomach thus collapsing it. The collapsed stomach will by means of further suction, become affixed to the distal end of the device. The stomach can then be conveniently rotated by turning the proximal end of the device which remains external to the patient. The method may still further comprise deflecting the device at an articulated joint which lies proximal to the distal length which may be formed into the reverse J-curvature. Such deflection of the distal end of the device to the left will expose the vessels and nerves of the lesser curvature. Deflection to the right will expose the spleen, kidney and adrenal gland. Inferior deflection will expose the esophageal hiatus and vagus nerves. Anterior deflection will expose the pancreas and the contents of the lesser sac. Superior deflection will expose the blood vessels between the transverse colon and stomach.

The device of the present invention comprises a shaft having a proximal end and a distal end, means on the shaft for selectively articulating a distal length of the shaft relative to a proximal length of the shaft, and means for selectively increasing the cross-sectional area of a terminal portion of the proximal length. In a preferred embodiment, the shaft comprises an internal spine having a deformable distal length and means at the proximal end of the shaft to deform such length, preferably into a reverse J-curvature. The shaft preferably further comprises an articulated junction defining a distal length and a proximal length, and the device may further comprise means actuable from the proximal end for deflecting the distal length relative to the proximal length. Conveniently, the deflecting means may comprise a cable eccentrically attached to the distal length and means at the proximal end of the device for applying axial tension on the cable.

The methods and devices of the present invention permit stomach retraction using an instrument which is contained solely within the esophagus and stomach and which does not need to enter the surgical field. The method and device are highly versatile, allowing the stomach to be retracted in a wide variety of configurations.

DESCRIPTION OF SPECIFIC EMBODIMENTS

Figure 1:
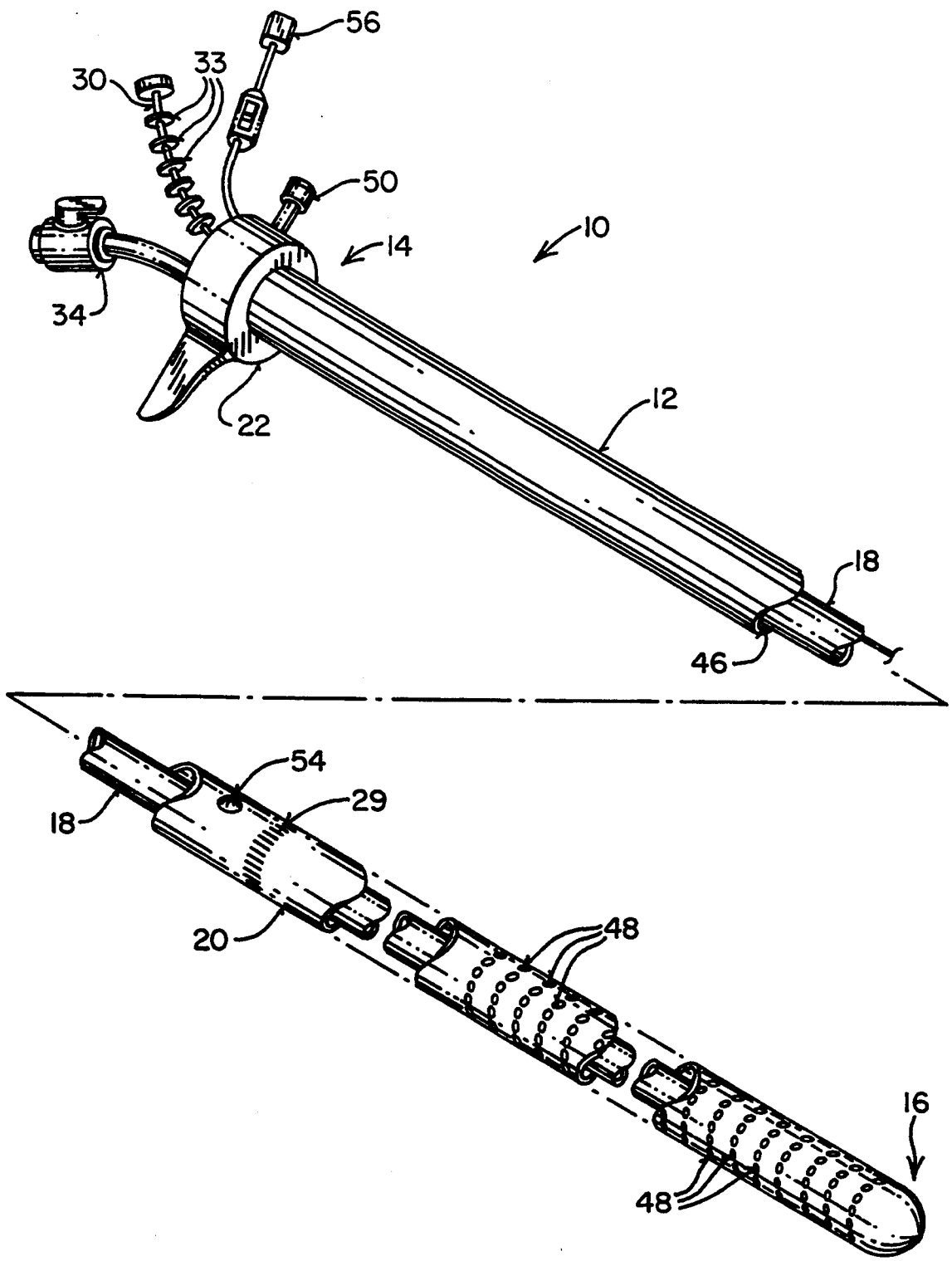
FIG. 1 is a perspective view of a transesophageal device for stomach retraction constructed in accordance with the principles of the present invention.

The methods and devices of the present invention are useful for performing stomach retraction in conjunction with a variety of surgical procedures in order to expose certain accessible organs and regions which would otherwise be obscured or blocked by the presence of the stomach. Organs which may be made accessible by stomach retraction include the spleen, colon, pancreas, kidney, adrenal gland, and the like. Exemplary surgical procedures which can be performed using the stomach retraction method of the present invention include diaphragmatic hernia repairs, Heller esophagogastric myotomies, highly selective vagotomies, gastrectomies, vertical banded gastroplasties, gastrojejunostomies, splenectomies, adrenalectomies, nephrectomies, transverse, splenic flexure, and descending colon resections, and the like. While the method and device of the present invention are particularly useful when performing such procedures by laparoscopy (or equivalent minimally invasive surgical technique utilizing a video monitor display), they are also useful for performing these and other techniques by conventional open surgical procedures performed through a major incision in the abdomen or elsewhere.

The device and method of the present invention will find particular use in performing laparoscopic gastroplastic procedures as described in detail in copending application Ser. No. 07/939,211, the full disclosure of which is incorporated herein by reference. In such procedures, the device and method of the present invention will be utilized to expose the lesser curvature of the stomach to permit clearing of the anterior and posterior branches of the gastric artery and vein, as will be described in detail hereinafter.

The device of the present invention will comprise a shaft having a proximal end and a distal end, where the shaft will be sufficiently soft and flexible to permit transesophageal introduction of the distal end to a patient's stomach. The shaft will be sufficiently long so that its proximal end will extend outward through the patient's mouth when the distal end has been fully inserted into the stomach, typically having a length in the range from about 90 cm to 120 cm. The diameter of the device shaft is not critical, typically being as small as possible consistent with the mechanical requirements described hereinafter. Typically, the diameter will be in the range from about 10 mm to 170 mm, with the diameter usually but not necessarily being uniform along the entire length of the shaft.

The shaft will include a proximal length, typically extending over the proximal 45 cm to 70 cm of the device, and a distal length, typically extending over the distal 35 cm to 55 cm of the device. The distal length of the shaft will lie within the patient's stomach when the device has been fully inserted, and the proximal length will extend through the esophagus and out from the patient's mouth in order to permit grasping and manipulation by the treating physician. The distal length of the shaft will be configurable to effect or assist in stomach retraction, while the proximal length will serve primarily to connect the distal length to a handle or other manipulation element which is connected to the proximal end of the device. Optionally, the distal length of the shaft may include a plurality of vacuum ports which may be connected to a vacuum source at the proximal end of the device in order to empty the stomach contents and collapse and affix the stomach onto the shaft in order to facilitate retraction and repositioning. In this way, the treating physician can perform a variety of specific stomach retraction procedures by reconfiguring the distal length of the shaft and/or physically translating or turning the entire catheter by manipulating the proximal handle.

The specific structure of the shaft can vary widely so long as it can perform the stomach retraction procedures described above and hereinafter. Conveniently, the shaft may comprise one or more tubular structures with a distal length having an expandable cross-sectional area. The expandable cross-sectional area may comprise an inflatable element which extends outward from the distal length, but will more usually comprise one or more deformable or deflectable portions which permit a desired reconfiguration after the distal length has been positioned within the stomach. In the specific embodiment which is described below, the proximal length will include both a deformable portion which may be bent into a reverse J-shaped curvature as well as an articulated joint between the distal length and proximal length which permits the distal length to be laterally, anteriorly, and posteriorly, deflected relative to the proximal length.

The shaft must have sufficient torsional rigidity in order to be able to transmit torque from the proximal end to the distal length in order to turn and otherwise reposition the stomach as just described. Such torsional rigidity can be achieved in a variety of ways. Conveniently, the shaft may comprise one or more tubular elements which are reinforced, typically by laminated braided layers, or the like.

Referring now to FIGS. 1–4, an exemplary transesophageal stomach retraction device 10 constructed in accordance with the principles of the present invention will be described. The device 10 comprises shaft 12 having a proximal end 14 and a distal end 16. The shaft 12 includes an internal spine 18 and an outer cover 20 which are both connected at their proximal ends to a handle 22. The entire device 10 can thus be manipulated by a treating physician who grasps the device by handle 22 while the remainder of the device has been inserted through the mouth and esophagus into the patient's stomach.

The internal spine 18 is a tubular member which provides the primary mechanical support for the shaft 12. Typically, the spine 18 is a tube formed of a polymeric material, more typically being formed from an extruded polymer such as polyethylene, polyurethane, polyvinylchloride, or the like. Frequently, the tubular member of spine 18 will be reinforced, such as with braided reinforcement, in order to enhance torsional rigidity without a substantial loss of axial flexibility. Specific methods for forming metal braid reinforced polymeric tubes are taught in U.S. Pat. No. 4,764,324, to Burnham, the full disclosure of which is incorporated herein by reference.

Figure 2:
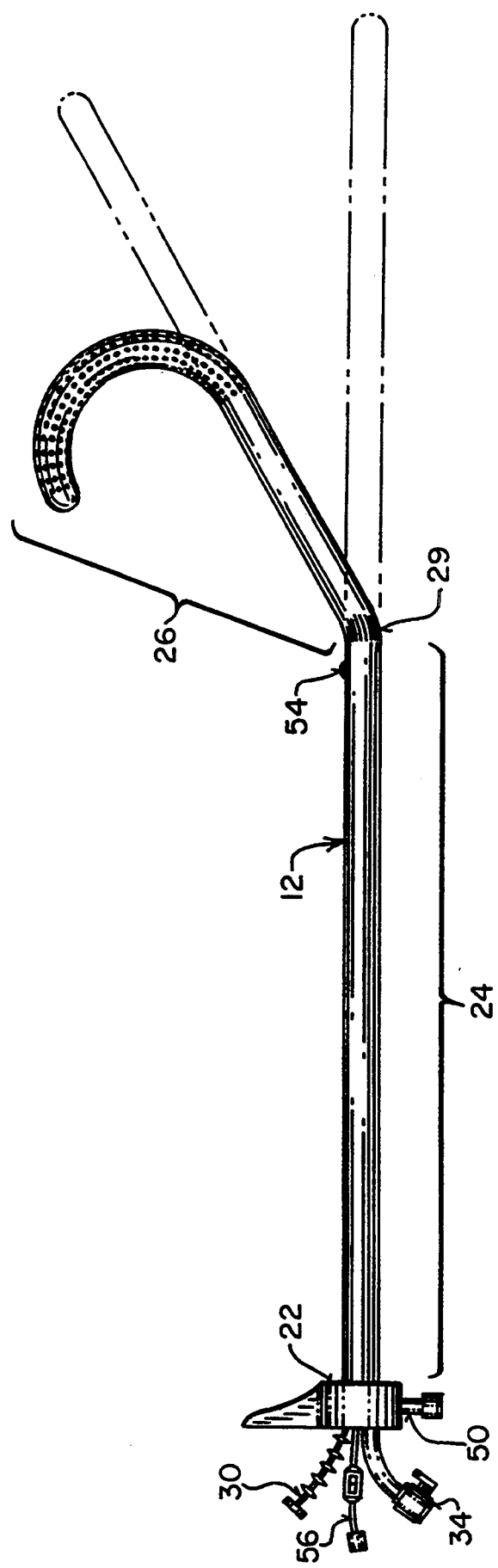
FIG. 2 is a side elevational view of the device of FIG. 1 illustrating the various configurations which may be assumed by the distal length of the device of FIG. 1.
Figure 3:
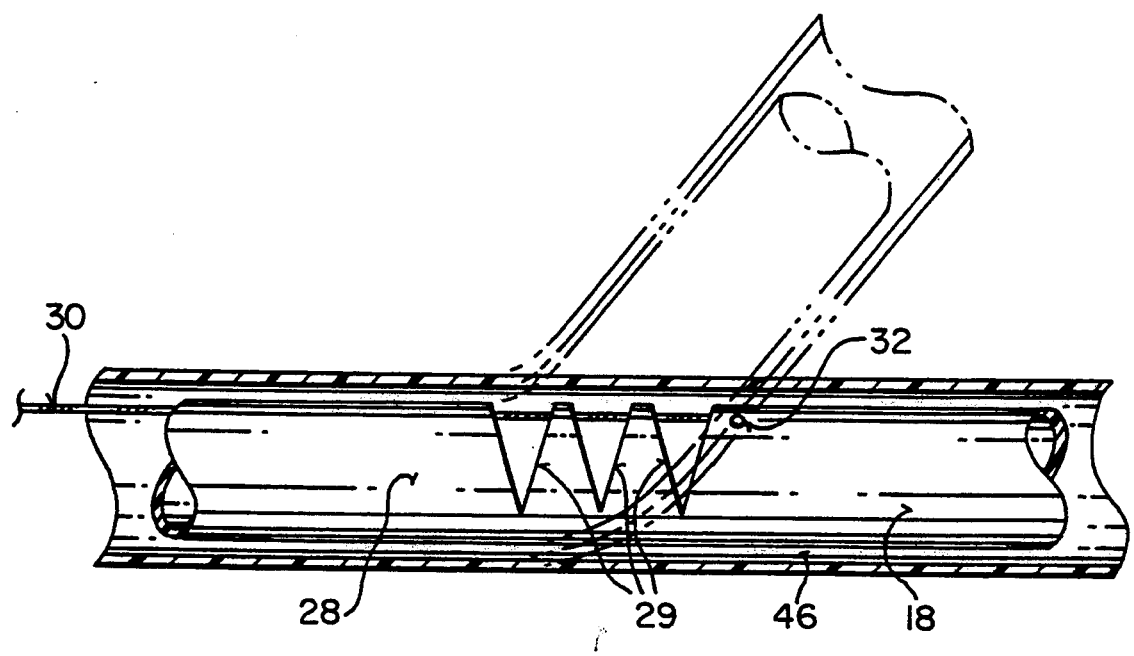
FIG. 3 is a detailed cross-sectional view of the device of FIG. 1 illustrating the articulated junction between the proximal length and the distal length, with the deflected configuration shown in broken line.

The internal spine 18 includes an articulated junction 28 (FIG. 3) which permits a distal length 26 of the shaft 12 to be laterally deflected relative to a proximal length 24 (FIG. 2). The suitable articulated junction 28 may be formed by placing a series of pie-shaped cutouts 29 in one side of the tubular member at the location where bending is desired, i.e. between the proximal length 24 and distal length 26. The internal spine 18 may then be deflected at the junction 28 by means of a cable 30 which is attached at location 32 on the distal side of the cutouts 29. Cable 30 extends from location 32 proximally outward through the handle 22. Thus, the distal portion 26 can be laterally deflected by pulling axially on cable 30 to collapse the pie-shaped cutouts 29 a desired amount. As illustrated, cable 30 includes a plurality of retaining bumps 33 at its proximal end which may be held in a retaining slot (not illustrated) in the housing 22 so that the lateral deflection may be maintained while the procedure is performed. Shaft 12 may be returned to its straightened configuration by releasing the cable 30 from the housing 22 so that the natural elasticity of the internal spine 18 straightens the shaft.

Figure 4:
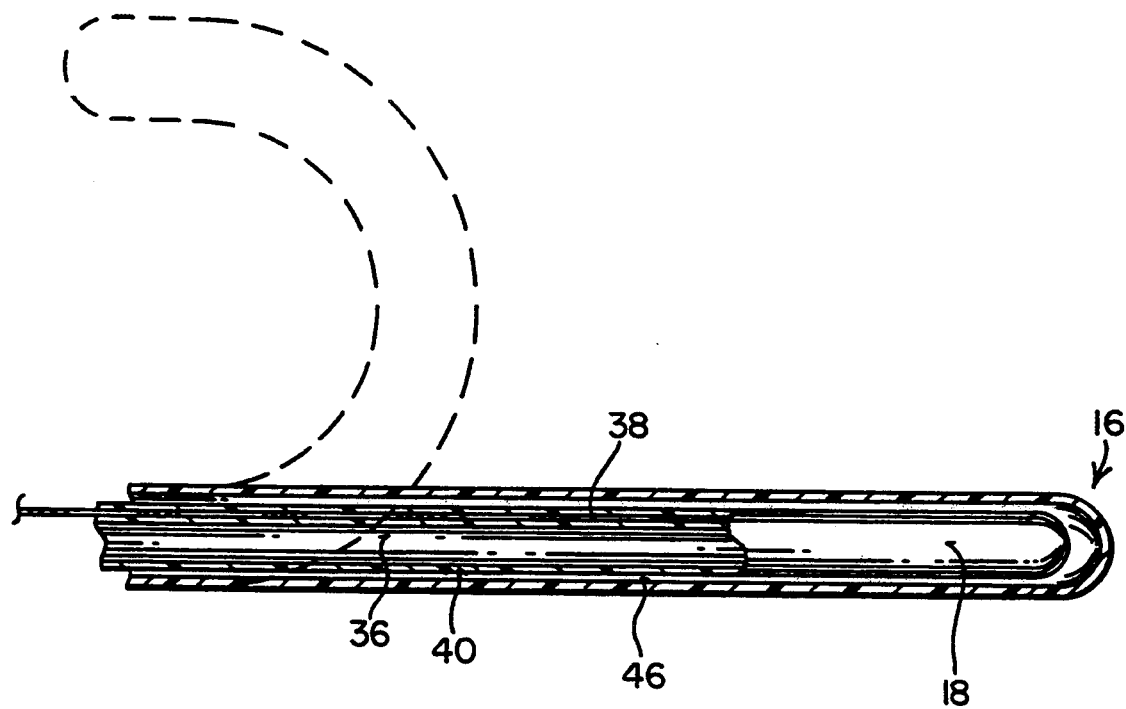
FIG. 4 is a detailed view of the distal length of the device of FIG. 1, shown with the device and its J-curvature in broken line.

Referring now to FIG. 4, the proximal portion of the proximal length 26 may be deformed into a reverse J-curvature by internal pressurization through a connector 34 extending from housing 22. Spine 18 has a hollow lumen 36 and is reinforced along one side by a reinforcement element 38. Typically, the wall 40 opposite the reinforcement element 38 will be thinned and free from any reinforcement so that it will be relatively resilient and "stretchable" when the spine 18 is internally pressurized. Thus, it will be appreciated that the length of the reinforcement element 36 is fixed, while the length of the opposite wall 40 may be expanded. In this way, internal pressurization will cause the desired J-curvature, as illustrated in solid line in FIG. 2 and broken line in FIG. 4. The pie-shaped cutouts 29 will of course be sealed to prevent loss of internal pressurization. It will be further appreciated that the remaining length of the internal spine 18 which lies proximal to the deformable tip section should be sufficiently strong and have sufficient hoop strength so that internal pressurization will cause no deformation.

The outer cover 20 lies coaxially over the internal spine 18 and is spaced-apart therefrom to define an annular lumen 46. A plurality of perforations 48 are formed over a portion of the distal length 26 of cover 20, typically over the portion which may be deformed in the J-curvature. Perforations 48 open from the exterior into the annular lumen 46, and a vacuum connector 50 is provided on the housing 22 to permit a vacuum to be drawn through the perforations. In this way, fluids and air may be withdrawn from the patient's stomach when the device 10 is in place. In particular, the inner stomach wall can be collapsed onto the exterior of the distal length 26 to facilitate manipulation of the stomach, as will be described in more detail hereinafter.

A light 54 is provided on the outer cover 20 at a location immediately proximal of the juncture created by cutouts 29. The light will typically be a light-emitting diode which is powered through a connector cord 56 passing out of housing 22. Alternatively, the light 54 may be provided using a fiber optic waveguide (not shown) which passes from the housing 22 to the location 54.

Figure 6:
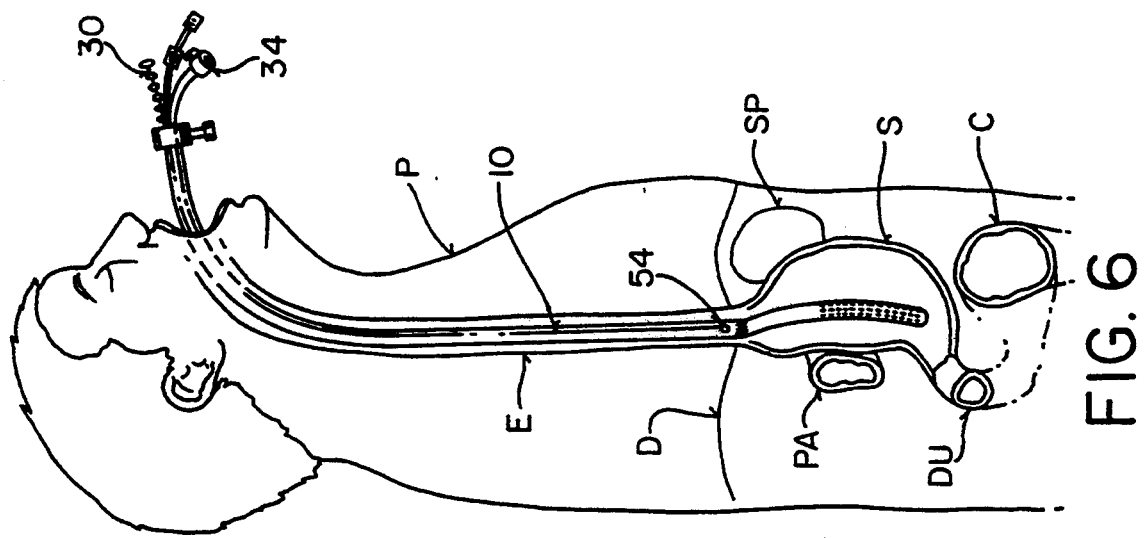
FIGS. 5-20 are schematic illustrations of the use of the device of FIGS. 1-4 in manipulating a patient's stomach in accordance with the principles of the method of the present invention.
Figure 5:
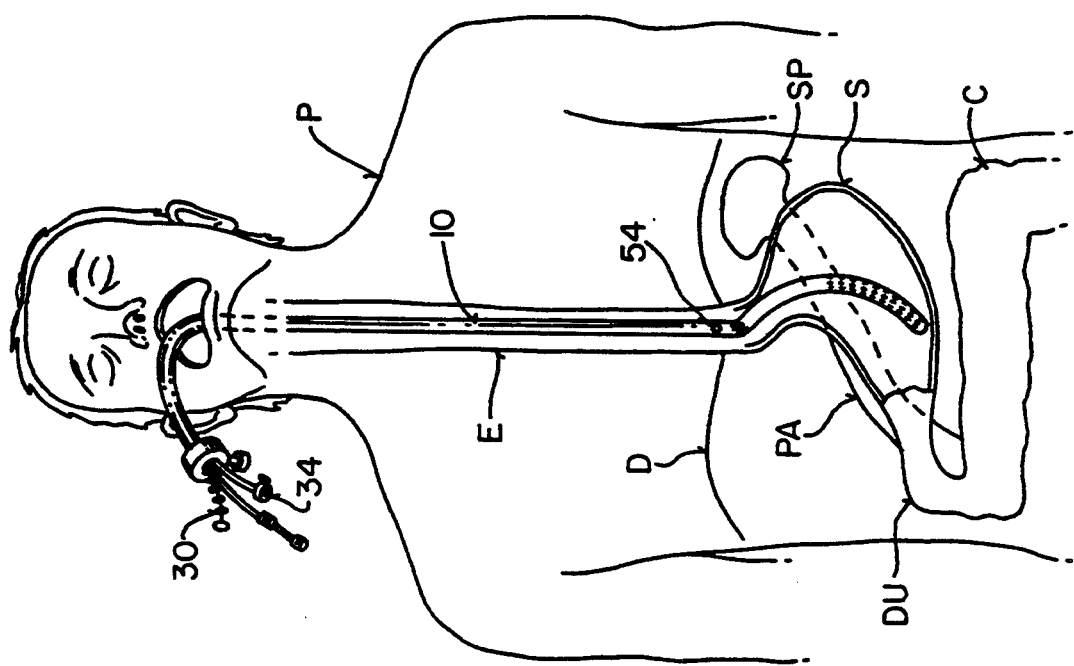

Referring now to FIGS. 5–20, methods according to the present invention utilizing the device 10 for manipulating the stomach S of a patient P will be described. The patient P is anesthetized, and access to the abdominal cavity is obtained by insufflation, umbilical trocar, and insertion of a laparoscope (not illustrated). Secondary trocars (not illustrated) are placed in the left upper quadrant, and the stomach S is retracted downward using conventional graspers. The device 10 is introduced into the patient's esophagus E through the mouth, and the blunt end is observed passing into the stomach by the treating physician through the video monitor attached to the laparoscope. Proper positioning of the device 10 within the stomach S can be confirmed by observing light 54 so that it transilluminates the distal esophagus. Device 10 is in the proper position and orientation when the light 54 is projecting anteriorly at the opening of the esophagus E into the stomach S. This position is illustrated in FIGS. 5 and 6. FIGS. 5 and 6 further illustrate the relative positions of the spleen SP, transverse colon C, duodenum DU, pancreas PA, and diaphragm D.

Figure 7:
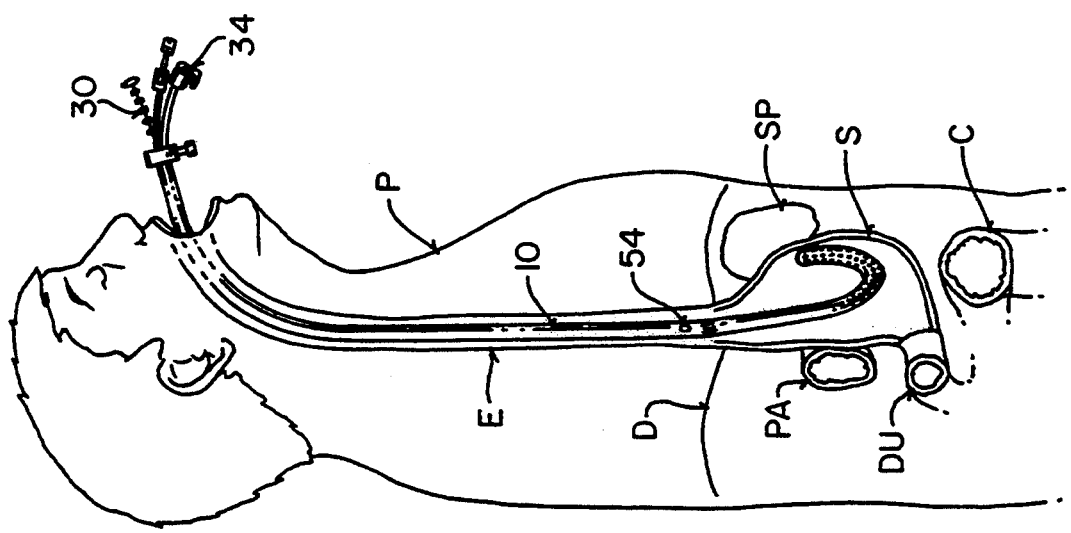
Figure 8:
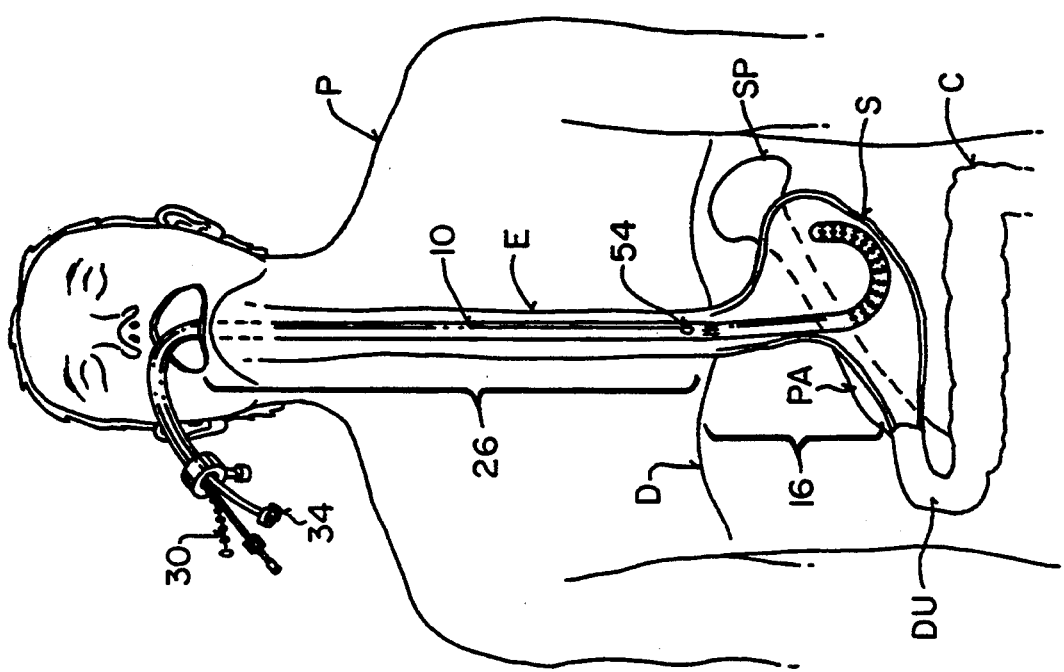

Referring now to FIGS. 7 and 8, the distal end 16 of device 10 is formed into a reverse J-shape by pressurizing the proximal length of 26 through connection 34. Usually, this manipulation is performed by a physician's assistant. The device 10 will be rotationally oriented so that the resulting J-shaped curl will extend to the patient's left, which curvature will tend to stretch the medial and lateral walls of the stomach S, usually called the lesser and greater curvatures, apart. The resulting repositioning of the stomach S will be of value in performing laparoscopic anterior seromyotomy which is commonly performed as part of a highly selective vagotomy ulcer prevention surgery.

Figure 9:
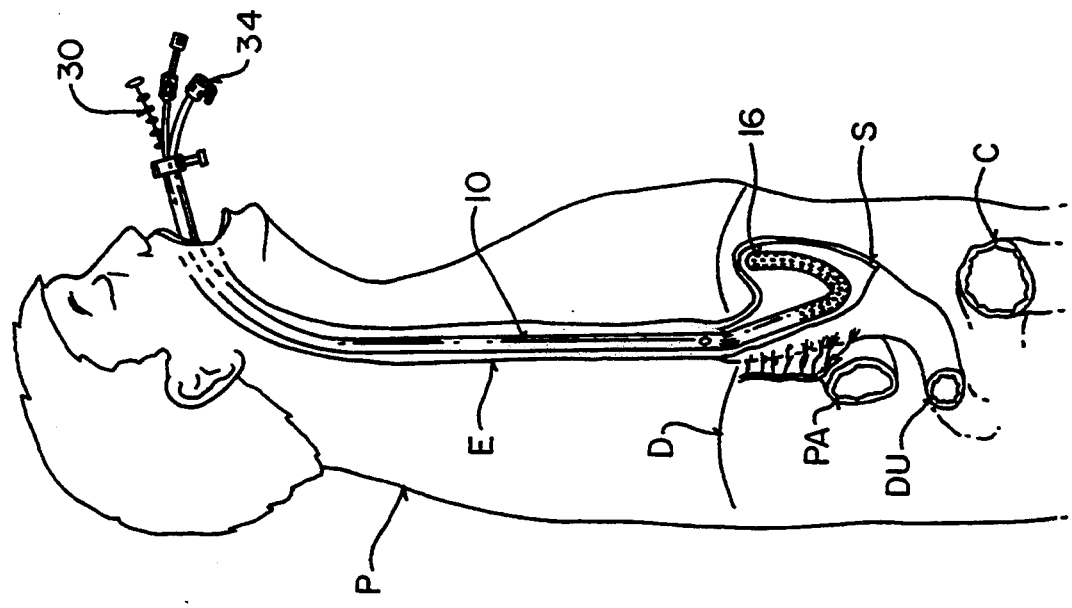
Figure 10:
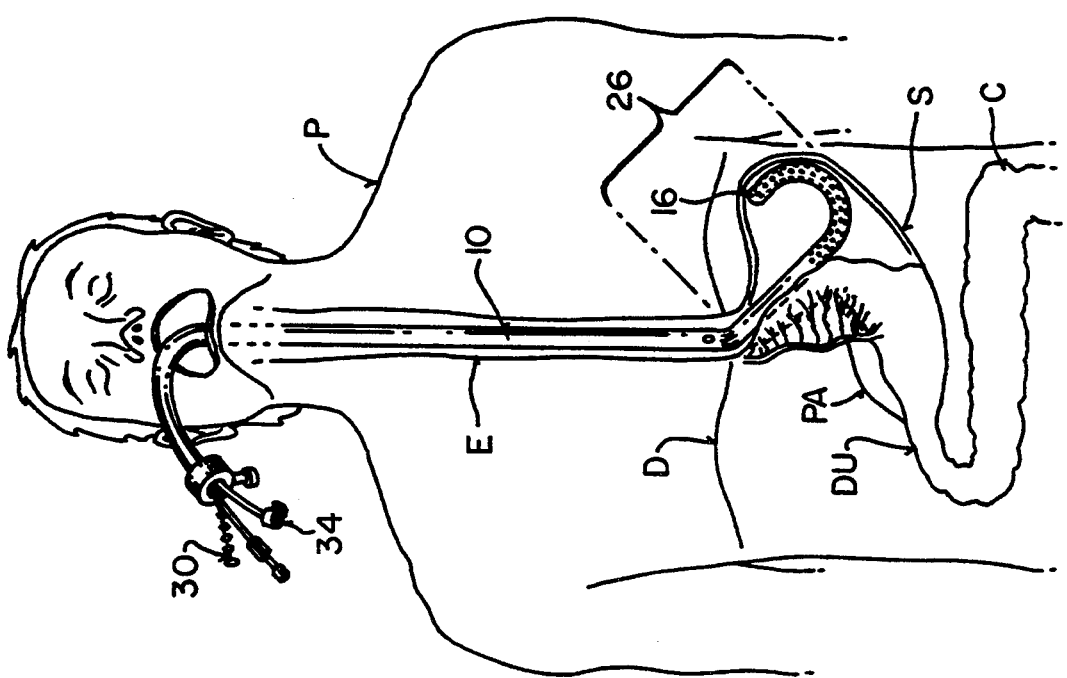

Referring now to FIGS. 9 and 10, distal portion 26 of retraction device 10 can be laterally displaced to the left by pulling axially on cable 30. The resulting shortening of cable 30 will cause the entire distal end 16 of device 10 to articulate about joint 29, preferably by 45° as best observed in FIG. 9. The J-shaped section 26 thus pulls the entire stomach to the left. Such pulling stretches the lesser curvature (medial site) of the stomach S as illustrated. The resulting tension on the blood vessels on the lesser curvature (the anterior branches of the left gastric artery) facilitates their dissection. Such repositioning of the stomach S will be of assistance in performing any laparoscopic gastric procedure calling for such dissection of the blood vessels.

Figure 12:
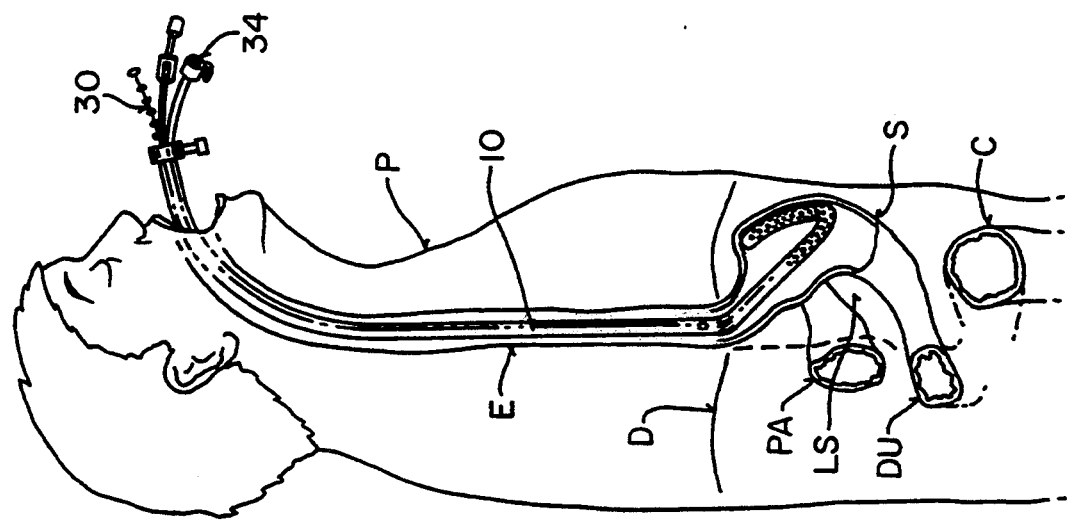
Figure 11:
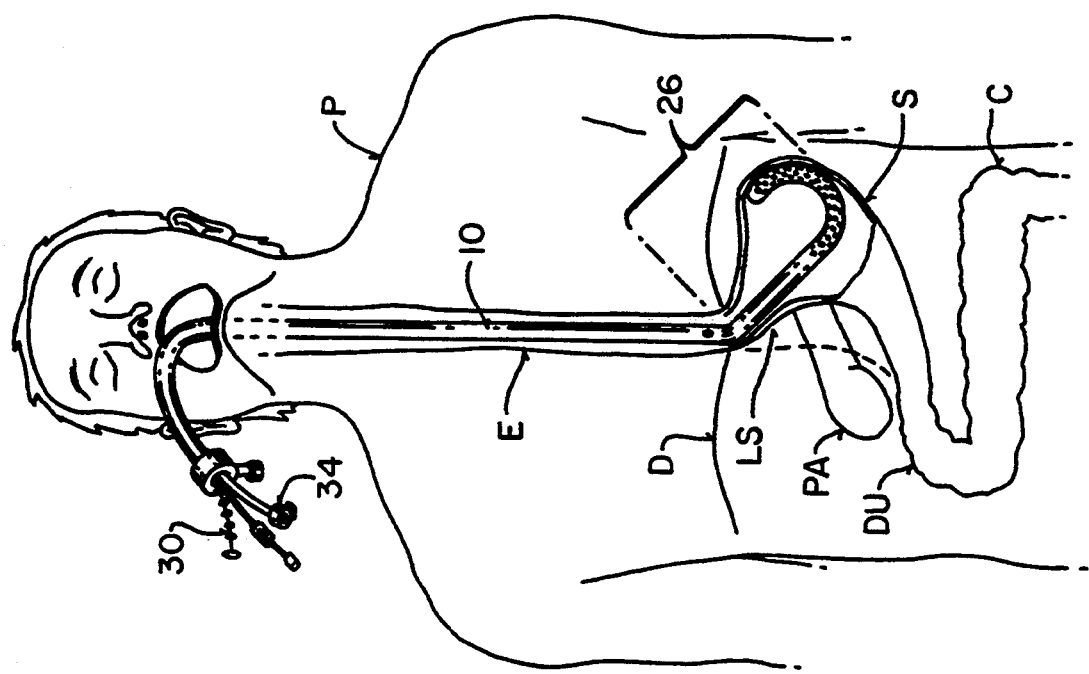

Referring now to FIGS. 11 and 12, the distal portion 26 of device 10 may be anteriorly displaced to pull the entire stomach S upward toward the anterior abdominal wall. Such repositioning of the stomach S exposes the lesser omental sac LS, which is the space posterior to the stomach S and anterior to the pancreas PA. Such repositioning of the stomach S would be useful to expose the lesser sac LS in a variety of procedures, such as a laparoscopic vertical banded gastroplasty, various procedures on the body and tail of the pancreas, separation of the stomach from the transverse and splenic flexure of the colon, and procedures which rely on access to the kidney, adrenal gland, renal vein, splenic vein, and abdominal aorta.

Figure 14:
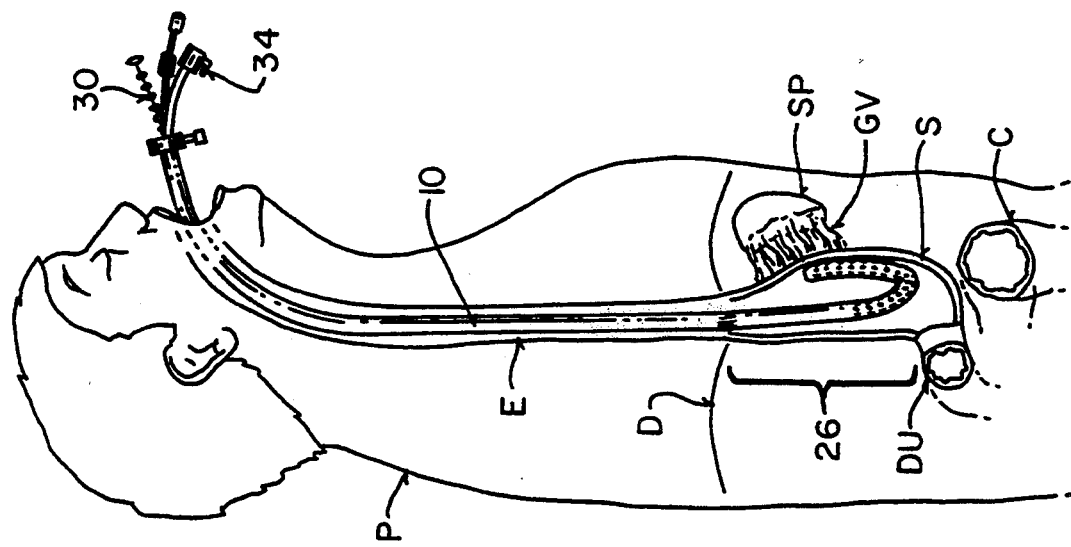
Figure 13:
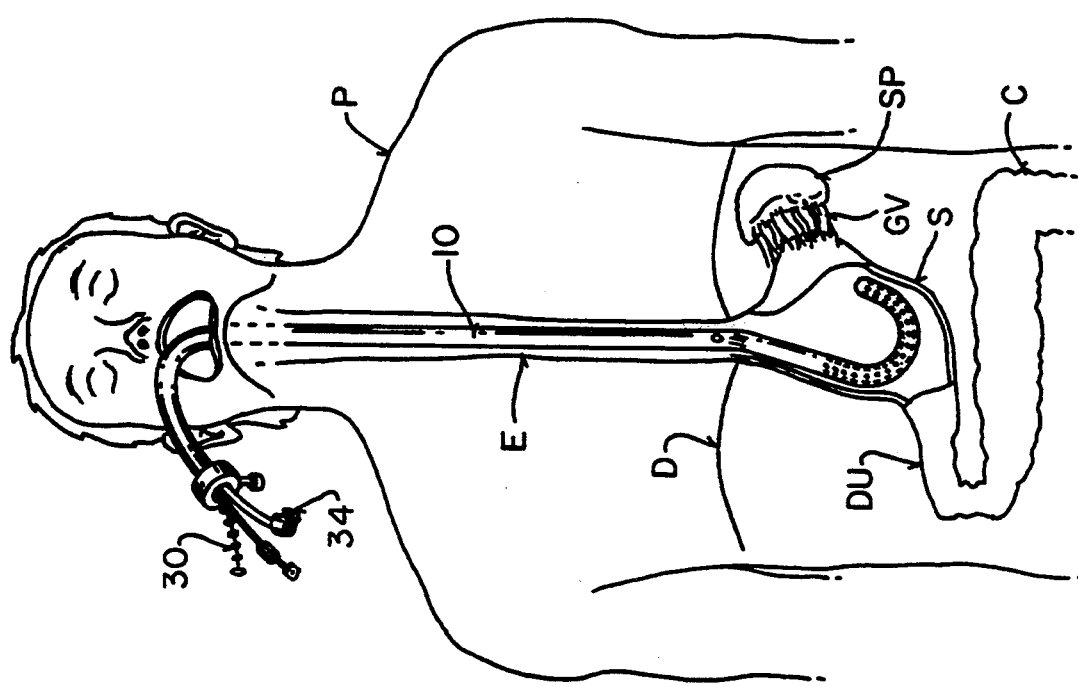

Referring now to FIGS. 13 and 14, the distal portion 26 of device 10 can be deflected immediately toward the patient's right side. Such deflection of the device 10 pulls the lesser curvature of the stomach S to the right. By applying a downward force on the stomach (which can be accomplished by rotating the device to urge the distal portion of the J-curvature downward), the short gastric vessels GV are stretched. The short gastric vessels GV connect the spleen to the greater curvature of the stomach, and such exposure facilitates performance of laparoscopic procedures, such as splenectomy, gastrectomy, Nissen diaphragmic hiatal hernia repair, as well as left kidney and left adrenal procedures.

Figure 16:
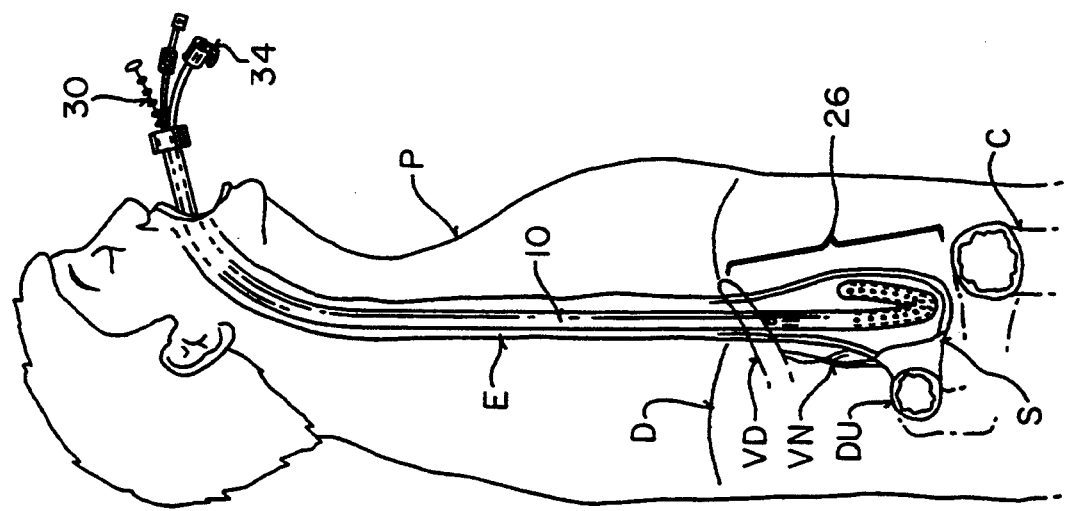
Figure 15:
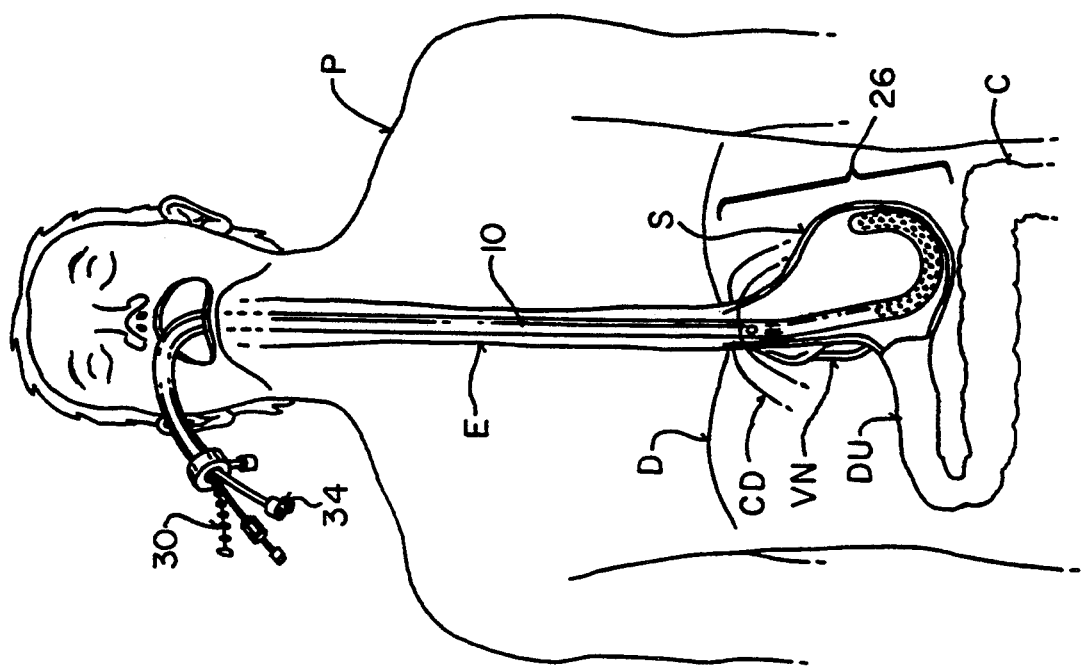

Referring now to FIGS. 15 and 16, downward pressure on the curved distal region 26 of device 10 can displace the entire stomach S inferiorly. Such downward pressure could be achieved by inserting the device 10 further into the patient's esophagus E and stomach S. Such further insertion would place the upper portion of the stomach S under tension and facilitate identification and dissection of anatomical features on the lower esophagus, the crus of the diaphragm D, the diaphragmic hiatus, the right vagus nerve, and the upper stomach. Such manipulation could aid in the performance of a laparoscopic procedure such as Nissen diaphragmic hiatal hernia repair, highly selective vagotomy, anterior seromyotomy, adrenalectomy, and splenectomy.

Figure 18:
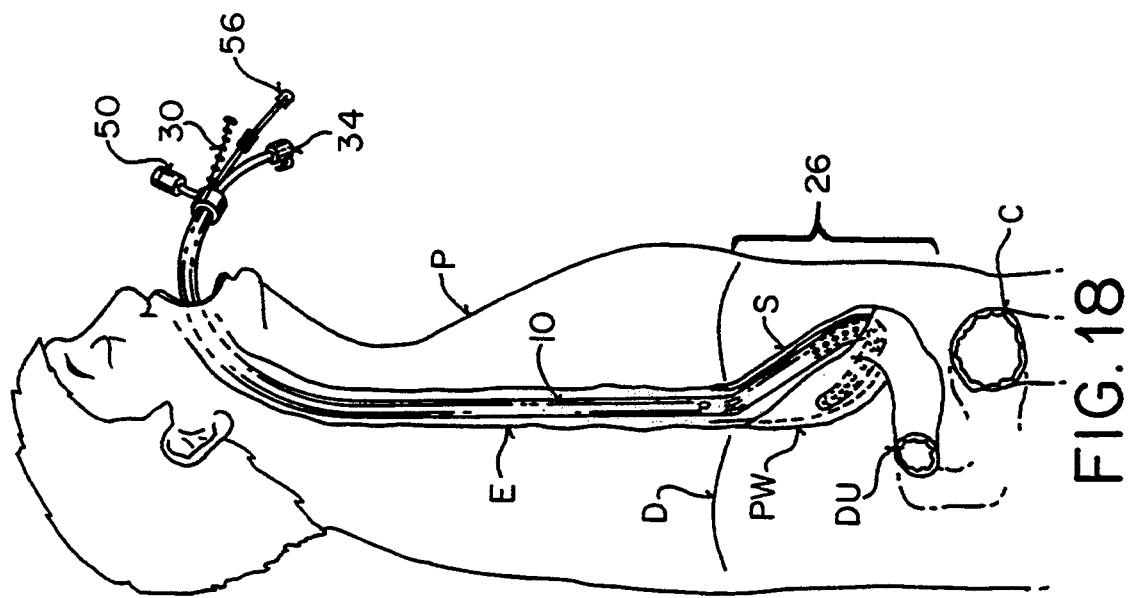
Figure 17:
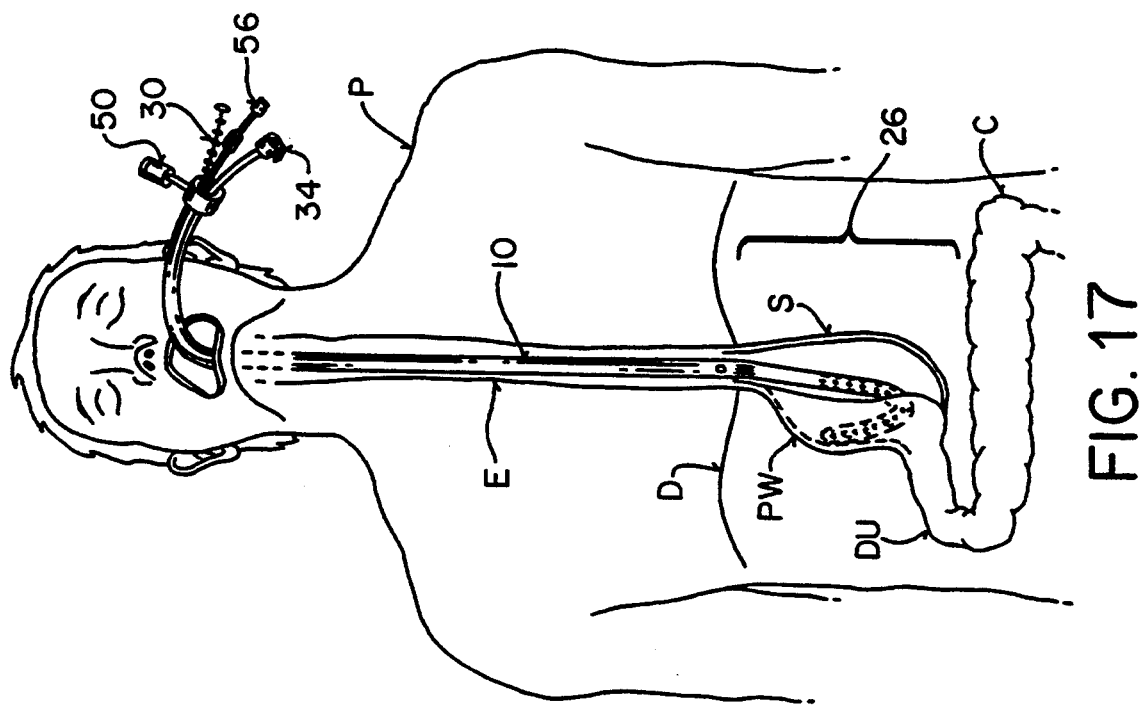

Referring now to FIGS. 17 and 18, the stomach S can be emptied and collapsed onto the distal region 26 of device 10 by applying a vacuum to port 50 and thus through perforations 48. After the stomach has been emptied and collapsed, continued adherence can be achieved by continuing with a low vacuum at port 50. The stomach can then be rotated by rotation of the proximal end of device 10 on the right side of the patient's mouth to the left side of the patient's mouth, by an angle from 0° to 120°. Such rotation will cause the lesser curvature, which is normally medial, to move to the left as the greater curvature rotates toward the midline behind. In this way, the back wall of the stomach S is brought into view, exposing the posterior branches of the left gastric artery. Such manipulation of the stomach S will be of benefit in the performance of a laparoscopic vertical banded gastroplasties and all other gastric operations that require access to the vessels of the posterior wall of the stomach.

Figure 20:
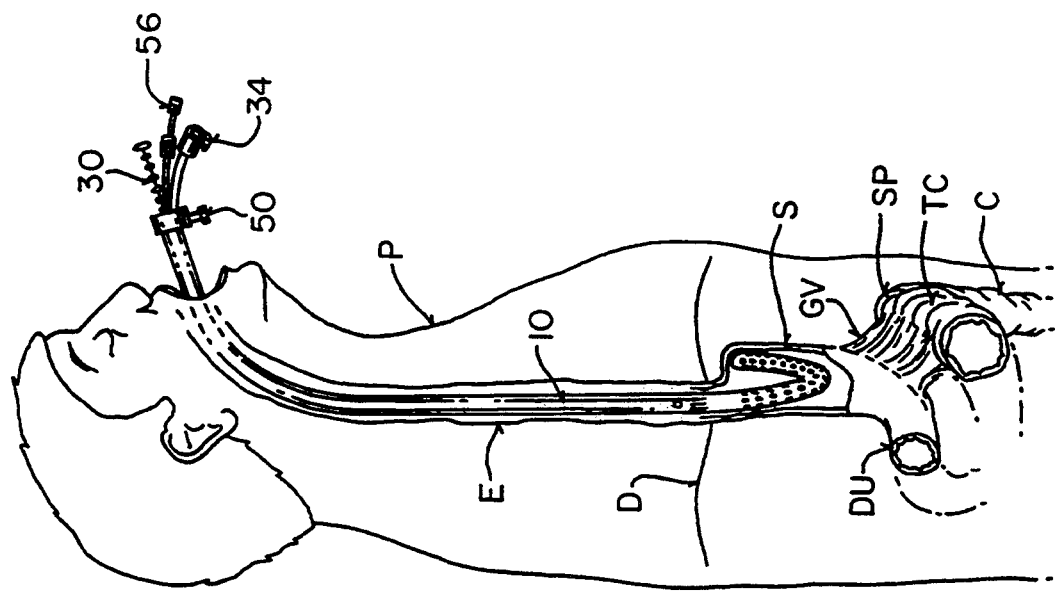
Figure 19:
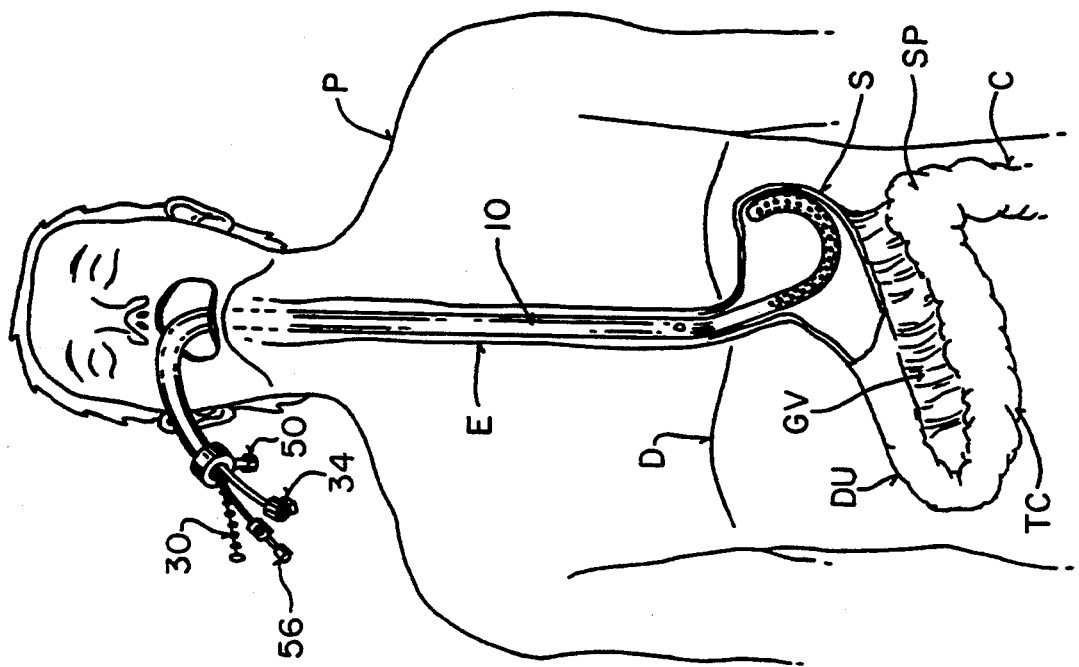

Referring now to FIGS. 19 and 20, the stomach S can be emptied and collapsed with the application of pressure at port 50, as described above. By then withdrawing device 10 a short distance outwardly from the esophagus E and stomach S, greater curvature of the stomach will be retracted superiorly toward the esophageal hiatus. Such manipulation will place the greater momentum, which is the connection between the transverse colon TC and the greater curvature of the stomach, on a stretch. Such manipulation facilitates dissection of the stomach, colon, and connecting blood vessels. It also permits access to the lesser sac, which is the space behind the stomach. Such manipulations facilitate performance of gastric surgery of any kind, colon resection, splenectomy, and pancreatic surgery.

Although the foregoing invention has been described in some detail by way of illustration and example, for purposes of clarity of understanding, it will be obvious that certain changes and modifications may be practiced within the scope of the appended claims. In particular, although the foregoing invention has been described in its principal application of retracting the stomach, the principles inherent in the device can also be used for retracting the colon by means of access through the anus to aid in the performance of laparoscopic surgery on this organ.

What is claimed is:

1. A method for performing a laparoscopic procedure in the region of a patient's stomach, said method comprising:

insufflating the abdomen to raise the abdominal wall over the stomach;

introducing a laparoscope into the region between the abdominal wall and the stomach;

viewing the region of the stomach through the laparoscope;

providing a device having a distal and proximal end with means for forming a J-shaped curvature in the distal end of the device from the proximal end of the device;

inserting a device through the patient's esophagus so that a distal end of the device lies within the stomach and a proximal end of the device extends outward from the patient's mouth;

manipulating the proximal end of the device to form the J-shaped curvature in the distal end of the device through the patient's esophagus to move the stomach and expose a region of or near the patient's stomach to the laparoscope; and, performing a procedure in the exposed region through an incision in the abdominal wall while viewing the region through the laparoscope.

2. A method as in claim 1, further comprising positioning the device within the esophagus and stomach by observing an illuminated light on the device through the tissue of the esophagus and stomach.

3. A method as in claim 1, further comprising increasing the cross-sectional area of the distal end of the device after inserting.

4. A method as in claim 3, further comprising deflecting an articulated distal length of the device to increase exposure of the lesser curvature of the stomach.

5. A method as in claim 3, further comprising applying a vacuum to a plurality of ports along the distal end of the device and thereafter manipulating the proximal end to turn the stomach and expose the posterior vessels of the lesser curvature of the stomach in a nontraumatic manner from the inside of the stomach for extended periods of time.

6. A method as in claim 1, wherein said performing a procedure in the exposed region through an incision in the abdominal wall while viewing the region through the laparoscope includes a procedure on the exterior of the stomach without perforating the stomach.

7. A method as in claim 6, wherein the proximal end of the device has been manipulated to position the distal end of the device so that the J-shaped curvature will engage the greater curvature of the stomach to expose the lesser curvature of the stomach in a non-traumatic manner for extended periods of time.

8. A method as in claim 6, wherein the procedure comprises clearing the anterior vessels of the lesser curvature of the stomach.

* * * * *